United States Patent [19]

Castellan et al.

[11] Patent Number: 5,120,866
[45] Date of Patent: Jun. 9, 1992

[54] PROCESS FOR OXIDIZING FLUORINATED OLEFINS AND CATALYSTS USEFUL FOR THE PURPOSE

[75] Inventors: Arsenio Castellan, Novara; Guglielmo Gregorio; Mario Padovan, both of Milan, all of Italy

[73] Assignee: Montedipe S.p.A., Milan, Italy

[21] Appl. No.: 686,290

[22] Filed: Apr. 16, 1991

Related U.S. Application Data

[63] Continuation of Ser. No. 507,019, Apr. 11, 1990, abandoned, which is a continuation of Ser. No. 219,889, Jul. 14, 1988, abandoned, which is a continuation of Ser. No. 887,816, Jul. 21, 1986, abandoned.

[30] Foreign Application Priority Data

Jul. 26, 1985 [IT] Italy ................... 21731 A/85

[51] Int. Cl.⁵ ........................... C07D 301/08
[52] U.S. Cl. ................................... 549/523
[58] Field of Search ..................... 549/259, 523

[56] References Cited

U.S. PATENT DOCUMENTS

| | | | |
|---|---|---|---|
| 3,775,438 | 11/1973 | Cavanaugh | 549/523 |
| 3,775,439 | 11/1973 | Atkins | 549/523 |
| 3,775,440 | 11/1973 | Cavanaugh et al. | 549/523 |
| 4,288,376 | 9/1981 | Ohsaka et al. | 549/523 |
| 4,562,269 | 12/1985 | Moorehead | 549/259 |

FOREIGN PATENT DOCUMENTS

| | | |
|---|---|---|
| 053804 | 4/1977 | Japan . |
| 053805 | 4/1977 | Japan . |
| 053806 | 4/1977 | Japan . |
| 134473 | 8/1982 | Japan . |

OTHER PUBLICATIONS

E. M. Flanigen et al, Nature, vol. 271, Feb. 9, 1978, pp. 512–516.

*Primary Examiner*—C. Warren Ivy
*Assistant Examiner*—Ba K. Trinh
*Attorney, Agent, or Firm*—Morgan & Finnegan

[57] ABSTRACT

A process for oxidizing fluorinated olefins to the corresponding epoxides by reacting a fluoroolefin with oxygen in a concentration, in the reaction mixture, ranging from 1 to 60% by volume, at a temperature up to 250° C. and in the presence of a catalyst consisting of porous silicon dioxide in a crystalline form, with a high purity degree and carrying metal oxides of the first transition series, or copper oxides or lanthanide oxides or mixtures thereof.

6 Claims, No Drawings

PROCESS FOR OXIDIZING FLUORINATED OLEFINS AND CATALYSTS USEFUL FOR THE PURPOSE

This is a continuation of co-pending application Ser. No. 07/507,019, filed on Apr. 11, 1990, now abandoned, which is a continuation application Ser. No. 07/219,889, filed Jul. 14, 1988, now abandoned, which is a continuation of Ser. No. 06/887/816, filed Jul. 21, 1986, now abandoned.

BACKGROUND OF THE INVENTION

1. Field of the invention

This invention relates to a process for oxidizing fluorinated olefins to the corresponding epoxides and to the catalyst useful for the purpose.

More in particular, the present invention relates to a process for oxidizing tetrafluoroethylene and hexafluoropropene, and to the relevant catalyst.

2. The prior art

Processes for oxidizing fluorinated olefins, for example tetrafluoroethylene and hexafluoropropene to the corresponding epoxides, such as the processes described in U.S. Pat. Nos. 3,775,438, 3,775,439 and 3,775,440, are known in the art.

According to what is described in this literature, hexafluoropropene and tetrafluoroethylene are oxidized with oxygen, either pure or mixed with inert gases, in the presence of a catalyst essentially consisting of silica.

The catalyst, which has a $SiO_2$ content ranging from 60 to 95% by weight, is used in different forms, particularly as a gel, as ground glass, as macroporous beads or also as sand.

These processes, although they permit to obtaining sufficiently high yields and conversions to epoxides, have very evident limits, which render them little suited to be utilized on a commercial scale. One of these limits is due to the catalyst life: in fact the catalyst becomes disactivated unless it is continuously treated with water or steam.

Another limit is due to the fact that the oxidation reaction, under certain conditions, requires a higher pressure than the atmospheric pressure or the use of high temperatures and in both cases the drawbacks are not negligible: in the former case, the hazard, in the latter case, the risk of using a temperature close to the epoxide decomposition temperature and, by consequence, of reducing the yield of finished product.

Subsequently, other processes for preparing in particular hexafluoropropene oxide have been proposed and are described in the published Japanese patent application Nos. 77/53804, 77/53805 and 77/53806.

Like in the other cases, oxidation occurs by direct contact between fluoroolefin and catalyst, but the catalyst is composed of a product based on silica, which carries promoters selected from transition metals, such as copper, chrome, manganese, iron, zinc, palladium and cerium.

Also in such cases, however, the shortcomings which highly limit the described processes, mainly as regards conversions and reaction yields, are still existing. The corresponding values are very low also owing to the too high reaction temperatures generally ranging from 250° to 300° C.

THE PRESENT INVENTION

Thus, it is an object of the present invention to provide a process for oxidizing fluorinated olefins which is not affected by the abovesaid drawbacks.

More in particular, it is an object of the present invention to provide a process for oxidizing fluorinated olefins $C_2$–$C_6$ and in particular tetrafluoroethylene and hexafluoropropene with high reagent conversions and yields and under reaction conditions which are consistent with the stability of the product.

Another object of the present invention is the catalyst suitable for the oxidation of fluoroolefins to epoxides.

The Applicant has now surprisingly found—and this is the object of this invention—that these and still other objects can be achieved by conducting the direct reaction between fluorinated olefin and oxygen in the presence of an oxidizing catalyst consisting of a crystalline form of porous silicon dioxide having a high purity degree and carrying oxides of metals of the first transition series or of lanthanides or mixtures thereof.

The term metals of the first transition series means the ones comprised, in the Periodic Table, between scandium and zinc. Preferred metals are copper, cobalt, cerium and chrome.

The process according to the present invention can be conducted either continuously or discontinuously.

According to a preferred embodiment, the oxidation reaction is conducted continuously by conveying the fluorinated olefin and the oxygen over a fixed or fluid catalytic bed and by keeping the reagents in contact for a time ranging from 100 to 1000 seconds.

Oxygen can be fed in the form of air or of another gas mixture containing at least 20% by volume of oxygen; the diluting gas is inert and can be, for example, helium or carbon dioxide.

Generally it is preferred to use pure oxygen, at a concentration, in the reaction mixture, ranging from 1 to 60% by volume.

Prior to the oxidation reaction, the catalyst is subjected to an activation step which can be accomplished by causing to flow on it either the reagents themselves or fluoroderivatives selected from dichlorodifluoromethane, tetrafluoromethane, hexafluoroethane, tetrafluoroethylene, hexafluoropropene, gaseous hydrofluoric acid or acid fluorides such as trifluoroacetylfluoride or carbonyl difluoride, either pure or diluted in inert gases, such as nitrogen, at temperatures from 0° to 300° C. depending on the activator type.

The oxidation reaction is conducted at atmospheric pressure or slightly above it, to overcome the pressure drops due to the catalytic bed, and at a temperature up to 250° C. In particular, if the produced epoxide is that of tetrafluoroethylene, the reaction temperature is lower, preferably below 50° C.; conversely, if the produced epoxide is that of a fluoroolefin having a number of carbon atoms from 3 to 6, the temperature preferably ranges from 50° to 250° C.

The epoxide so obtained can be recovered from the reaction mixture according to any known methods, such as distillation or washing.

A further object of the present invention is the catalyst used in this process.

Said catalyst is a material consisting of a carrier additioned with metal oxides, which exhibits excellent catalytic properties in the oxidation reactions, in particular in the oxidation reactions of fluoroolefins to epoxides.

The carrier is a crystalline form of porous silicon dioxide at a high purity degree, in particular with an aluminum content in a concentration below 0.1% by weight, and characterized by a X-ray diffraction pattern (Cu K $\bar{\alpha}$) with the following main reflection angles: $2\theta = 7.94°; 8.85°; 23.08°; 23.94°$.

The structure of the pure crystalline phase is porous with regular pores; such characteristic is evidenced by the specific surface values determined by absorption of nitrogen, such surface being attributable for over 50% to pores with an average diameter below 1 nm.

The total surface area ranges from 300 to 600 m²/g

The morphology of the crystallites is variable: the individuals appear in the octahedral or prismatic form with geminate prisms having an average size above 300 nm, and in any case easy to be distinguished from any other amorphous materials by means of electronic scanning microscopy.

Said carrier can be prepared according to known methods, as is described in Nature vol. 271 page 512 (1978), or is commercially available under the trademark SILICALITE ®.

The promoters, which consist of oxides of metals of the first transition series, i.e. those comprised, in the Periodic Table of elements, between scandium and zinc, or of lanthanides or of mixtures thereof, are additioned to the carrier by impregnating same either with the oxide or with any salt provided it is capable of decomposing by calcination in order to give rise to the corresponding oxide.

The promoters can be carried in amounts even higher than 40% by weight and, according to a preferred formulation of the catalyst object of the present invention, amounts in the range of from 1 to 30% by weight are utilized.

Any metal oxide of the above-cited group is capable of promoting the oxidation reaction of fluorinated olefins, however, preferred metal oxides are those of copper, cobalt, cerium and chrome.

The carrier impregnated with the transition metal salt is calcined in oven at temperatures ranging from 300° to 800° C., and is then subjected to an activating treatment as described hereinbefore.

A few illustrative but not limitative examples are given hereinafter in order to facilitate the comprehension of the present invention and the practising of same.

EXAMPLE 1

90 g of commercial SILICALITER ® (S-115 Union Carbide) were impregnated with 39 ml of an aqueous solution containing 18.6 g of $Cu(NO_3)_2.3H_2O$.

After impregnation, the impregnated catalyst was permitted to digest during 4 hours at room temperature, whereafter it was dried at 120° C. for 16 hours.

It was calcined at 500° C. for 4 hours in air, whereupon 4.5 g of an inert binder (Bentonite) were added and the whole was kneaded with 45 ml of distilled water.

It was dried at 120° C. for 16 hours and calcined at 540° C. for 2 hours in air. At least, the catalyst was ground and subjected to screening: the 32-80 mesh fraction was collected and definitively activated at 100° C. in a nitrogen stream containing 0.1% of hydrofluoric acid, during 5 hours.

On the spectrophotometric analysis (X-ray) the catalyst exhibited the following reflexes attributable to copper oxide:

$2\theta(Cu\ K\ \bar{\alpha}) = 38.75°; 36.60°; 48.97°$ besides the following, much more intense reflexes of the crystalline silica used as carrier:

$2\theta = 7.94°; 8.85°; 23.08°; 23.94°$.

30 g of the catalyst so prepared were introduced into a cylindrical 50-cc reactor made of Incoloy and externally heated.

The reactor was heated to 170° C. and a gaseous mixture of hexafluoropropene and oxygen in the ratio 90:70, namely 90 cc/h of hexafluoropropene and 70 cc/h of oxygen, was fed.

After about 1 hour the temperature was adjusted at 160° C. (maximum temperature along the catalytic bed). The outflowing gases were subjected to gas chromatographic analysis and their composition resulted to be the following: $O_2 = 14.1\%$; $CO_2 + COF_2 = 21.8\%$; $C_3F_6O = 21.1\%$; $C_3F_6 = 30.6\%$.

The resulting balance was corresponding to a conversion of 41.3% of the perfluoropropene with 75.6% of selectivity in epoxide.

After a 27-hour run, the gas composition was slightly varied as follows : $O_2 = 17\%$; $CO_2 + COF_2 = 23.7\%$; $C_3F_6O = 21.8\%$; $C_3F_6 = 35.2\%$, which was corresponding to a conversion of 45.5% of the hexafluoropropene with a selectivity of 74.5% in epoxide.

EXAMPLE 2

A flow consisting of 180 cm³/h of $C_3F_6$ and 140 cm³/h of $O_2$ was made to pass over 30 g of catalyst prepared according to the procedure of example 1 but in sizes of a mean diameter of 2 mm and activated for 3 hours with a nitrogen flow containing 0.5% of hydrofluoric acid, while the temperature was maintained on the average at 140° C. and not exceeding 147° C.

After 4 hours, the conversion and the selectivity were stabilized on practically constant values, i.e. a conversion of about 30% and a selectivity in $C_3F_6O$ higher than 77% from the 5th to the 50th hour of run.

A typical analysis of the outflowing gases after 43 h and 30 minutes was the following: $O_2 = 20.4\%$; $CO_2 + COF_2 = 11.7\%$; $C_3F_6O = 17.5\%$; $C_3F = 50.1\%$, corresponding to a conversion of 29.7% and to a selectivity of 82.6%.

After an eighty-hour run the catalyst was cooled and discharged. The sample, subjected to X-ray analysis, still revealed the reflexes of the starting SILICALITE with an intensity comparable to that of the starting sample.

EXAMPLE 3

3.5 g of a catalyst prepared as in example 1 (size: 32-80 mesh) were introduced into a 10-cc microreactor made of Incoloy.

The reactor was heated to 200° C. and a mixture consisting of 90 cc/h of hexafluoropropene and 70 cc/h of oxygen was made to flow on the catalytic bed so prepared.

After 1 hour the heating was adjusted in such manner that in the warmest point of the catalytic bed the temperature was of 200° C.

A practically constant conversion of the gas was observed and after a 14-hour run the analysis was as follows: $O_2 = 25.16\%$; $CO_2 + COF_2 = 9.8\%$ $C_3F_6O = 9.7\%$; $C_3F_6 = 53.7\%$, what was corresponding to a conversion of 19.15% and to a selectivity of 75.9%.

EXAMPLE 4

A catalyst was prepared under the same conditions described in example 1, except for the employed amount of Cu(NO$_3$)$_2$.3H$_2$O, that in the present case was of 3.7 g.

The final activation was carried out at 100° C. in a nitrogen stream containing 0.5% of hydrofluoric acid, during 1 hour.

3.5 g of the catalyst so prepared were introduced, in a size of 32-80 mesh, into a 10-cc microreactor made of Incoloy.

The reactor was heated to 200° C. and a mixture of 90 cc/h of hexafluoropropene and 70 cc/h of O$_2$ was conveyed thereinto.

The composition of the outflowing gases stabilized, after 2 hours, at a stable value and after 7 hours was as follows:

O$_2$=8%; CO$_2$+COF$_2$=16.5%; C$_3$F$_6$O=13.5%; C$_3$F$_6$=52.0%, what was corresponding to a conversion of 27% and to a selectivity of 69%.

EXAMPLE 5

10 g of a catalyst, in a size of 32-80 mesh, consisting of cobalt oxide on silicalite, prepared as in example 1 but using, however, cobalt nitrate instead of copper nitrate with the same amount of metal in gram atoms, were introduced into a 20-cc microreactor. It was heated to 230° C. and a mixture consisting of 90 cc/h of C$_3$F$_6$, 70 cc/h of O$_2$ and 30 cc/h of N$_2$ was sent thereinto.

The regular operating conditions were reached after a few hours, and the temperature was stabilized at 180° C. with a conversion of about 30%.

After a 6-hour run the conversion was stable and the outflowing mixture exhibited the following composition:

O$_2$+N$_2$=48.3%; CO$_2$+COF$_2$=4.2%;
C$_3$F$_6$O=12.4%; C$_3$F$_6$35.5%.

what was corresponding to a conversion of 31% and to a selectivity of 74.7% to epoxide.

EXAMPLE 6

3.5 g of a catalyst in a size of 32-80 mesh, consisting of cerium oxide on silicalite, prepared as in example 1, but using cerium nitrate in the place of copper nitrate, with the same amount of metal in gram atoms, were introduced into a 10-cc microreactor.

It was heated to 230° C. and a mixture of 90 cc/h of C$_3$F$_6$70 cc/h of O$_2$+30 cc/h of N$_2$ was made to flow thereinto during half an hour, whereafter the temperature was gradually lowered.

Regular operating conditions were reached at 195° C. and at this temperature a quite stable conversion was observed.

After 4 hours, an analysis of the outflowing gases revealed the following compositions:

O$_2$+N$_2$=38%; CO$_2$+COF$_2$=14.8%;
C$_3$F$_6$O=8.6%; C$_3$F$_6$=36.6%.

The conversion was of 27.9% and the selectivity of 61.2%.

EXAMPLE 7 (comparative test)

90 g of a commercial activated carbon designated as KAS/S HYDRO-LINE were ground and screened and the 32-80 mesh fraction was collected.

It was impregnated with an aqueous solution containing 9 g of Cu(CH$_3$COO)$_2$.H$_2$O by means of the double-impregnation technique. It was dried at 100° C. for 16 hours in air and it was calcined at 300° C. during 4 hours in nitrogen, then at 200° C. during 4 hours in air.

3 g of the catalyst so prepared were introduced into a 10-cc microreactor.

It was heated to 100° C. and a mixture of 90 cc/h of hexafluoropropene and 70 cc/h of oxygen was made to flow thereinto.

During the test, the temperature was brought from 100° to 200° C. The conversion of hexafluoropropene was in any case practically complete; the outflowing gases revealed no traces of hexafluoropropene epoxide but of other oxidation and pyrolysis products such as COF$_2$, CO$_2$, CF$_4$, CF$_3$COF, C$_2$F$_4$, cyclic C$_3$F$_6$ and other high-boiling products.

EXAMPLE 8 (comparative test)

50 g of commercial SiO$_2$ sol designated as Ketjensol were additioned with 50 ml of distilled water.

It was acidified with dilute HNO$_3$ up to a pH =6, and 4 g of Cu(NO3)$_2$.3H$_2$O were added to such solution.

Precipitation was carried out with an aqueous solution of KOH at 10%. It was filtered, repeatedly washed and dried at 120° C./16 h in air. It was calcined at 500° C. during 4 hours in air, whereafter the catalyst was subjected to grinding and to screening, and the 32-80 mesh fraction was collected.

3.5 g of the catalyst so prepared were introduced into a 10-cc microreactor. A flow of 90 cc/h of hexafluoropropene and 70 cc/h of oxygen was made to pass over this catalytic bed, while the reactor was heated up to 300° C. At 300° C. the conversion begun and after 1 hour the temperature was decreased to 160° C., whereafter it was maintained constant.

The outflowing gases were almost exclusively composed of the unaltered reagents. Now it was heated to 210° C.; in such way it was possible to observe the following composition of the reacted mixture: CO$_2$+COF$_2$=10.2%; O$_2$=36.5%; C$_3$F$_6$=51.8%, with traces of epoxide. The conversion was of 15%, but the selectivity for epoxide was lower than 1%.

EXAMPLE 9 (comparative test)

A catalyst consisting of copper carried on a zeolite containing aluminium was prepared by ionic exchange with copper nitrate on synthetic Fujasite (LZY-52 available from Union Carbide). The resulting product was calcined at 540° C. and subjected during 1 hour to a nitrogen stream at 100° C. which contained 0.1% of hydrofluoric acid.

On 2.4 g of said catalyst (32-80 mesh) there were made to pass 180 cm$^3$/h of C$_3$F$_6$ and 40 cm$^3$ h of O$_2$ at an initial temperature of 200° C.

After 3 hours at 200° C., the outflowing gas had the following composition:

O$_2$=23.6%; CO$_2$=14.1%; C$_3$F$_6$O=nihil;
C$_3$F$_6$=62.0%.

The temperature was then lowered to 150° C. with the same gas flow, and the following composition of the outflowing gas was observed:

$O_2 = 26.0\%$; $CO_2 = 1.15\%$; $C_3F_6O = 0.15\%$; $C_3F_6 = 71.2\%$.

After further 3 hours of run under these conditions, it was cooled down and the catalyst was discharged: the weight thereof resulted to be increased by 17% in consequence of the absorbed bed fluorine, while the X-ray analysis revealed that the crystalline structure of the starting Fujasite was for the most part no longer present, thus giving rise to an amorphous material.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A process for oxidizing tetrafluoroethylene or hexafluoropropylene to the corresponding epoxide comprising flowing a mixture of gaseous tetrafluoroethylene or hexafluoropropylene and oxygen at a temperature below 50° C. when starting from tetrafluoroethylene and at a temperature ranging from 50° C. to 250° C. when starting from hexafluoropropylene, over a catalyst bed, said catalyst consisting essentially of a crystalline form of a porous silicon dioxide with an aluminum content lower than 0.1% by weight, having an X-ray diffraction pattern having the following main reflection angles $2\theta = 7.94°$, $8.35°$, $23.08°$, $23.94°$, and carrying an oxide of copper, cobalt, cerium or chromium, wherein the catalyst, prior to the oxidation step of converting the tetrafluoroethylene or hexafluoropropylene to the corresponding epoxide, is subjected to an activation step accomplished by flowing over said catalyst a fluoroderivative selected from the class consisting of dichlorodifluoromethane, tetrafluoromethane, hexafluoroethane, tetrafluoroethylene, hexafluoropropylene, gaseous hydrofluoric acid, trifluoroacetylfluoride, and carbonyldifluoride, either pure or diluted with an inert gas, at a temperatures ranging from 0° to 300° C.

2. A process according to claim 1 in which the fluoroderivative is gaseous hydrofluoric acid.

3. A process according to claim 1, in which the mixture of tetrafluoroethylene or hexafluoropropylene and oxygen contains from 1 to 60% by volume of oxygen.

4. A process according to claim 1, in which the oxygen is fed to the mixture of tetrafluoroethylene or hexafluoropropylene and oxygen in the form of a gaseous mixture containing at least 20% by volume of oxygen.

5. A process according to claim 1, in which the reaction is conducted with contact times ranging from 100 to 1,000 seconds.

6. A process as defined in claim 1, in which the inert gas is nitrogen.

* * * * *